United States Patent [19]

Saito et al.

[11] Patent Number: 4,612,385
[45] Date of Patent: Sep. 16, 1986

[54] PROCESS FOR THE PREPARATION OF PHENYL N-(2-BIPHENYLYLSULFONYL) CARBAMATE

[75] Inventors: Junichi Saito, Mitaka; Tatsuo Tamura, Hamura, both of Japan

[73] Assignee: Nihon Tokushu Noyaku Seizo K.K., Tokyo, Japan

[21] Appl. No.: 804,207

[22] Filed: Dec. 3, 1985

[30] Foreign Application Priority Data

Dec. 6, 1984 [JP] Japan ................. 59-256546

[51] Int. Cl.$^4$ .......................................... C07C 143/83
[52] U.S. Cl. ................................................. 560/12
[58] Field of Search ........................................ 560/12

[56] References Cited

U.S. PATENT DOCUMENTS

| | | | |
|---|---|---|---|
| 3,590,074 | 6/1971 | Heiss | 560/132 |
| 3,649,674 | 3/1972 | Hoyer | 560/159 |
| 3,933,894 | 1/1976 | Stephens | 560/12 |
| 4,097,676 | 6/1978 | Romano | 560/137 |
| 4,230,874 | 10/1978 | Pallos | 560/12 |
| 4,537,986 | 8/1985 | Reissenweber | 560/132 |

FOREIGN PATENT DOCUMENTS 557074 10/1957 Belgium ................. 560/12

OTHER PUBLICATIONS

Specification, Nit 179 corresponding to Japanese Patent Application No. 70909/1984.

Primary Examiner—Michael L. Shippen
Attorney, Agent, or Firm—Sprung, Horn, Kramer & Woods

[57] ABSTRACT

The invention relates to a process for the production of phenyl N-(2-biphenylylsulfonyl) carbamate represented by the general formula

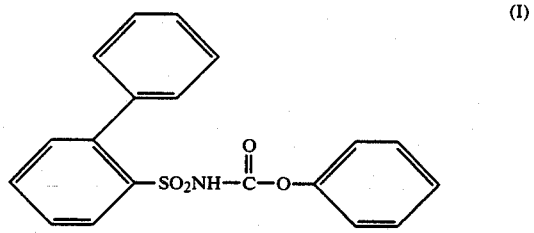

(I)

by reacting 2-phenylbenzene sulfonamide represented by the general formula

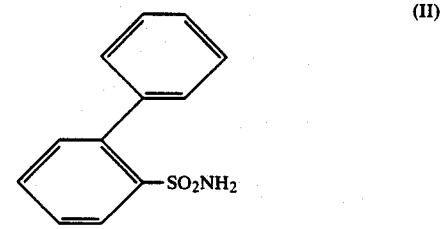

(II)

with diphenyl carbonate represented by the general formula

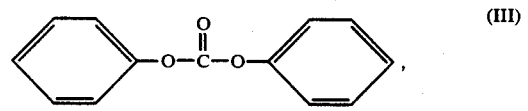

(III)

which is characterized in that said reaction is carried out in the presence of an alkali metal hydroxide and an aprotic solvent at temperatures between about 20° C. and about 60° C.

10 Claims, No Drawings

PROCESS FOR THE PREPARATION OF PHENYL N-(2-BIPHENYLYLSULFONYL) CARBAMATE

The present invention relates to an improved process for the preparation of the known phenyl N-(2-biphenylylsulfonyl) carbamate by reacting 2-phenylbenzene sulfonamide with diphenyl carbonate under certain specific reaction conditions.

The prior art (Japanese Patent Application No. 70909/1984) also discloses a process for the preparation of said phenyl N-(2-biphenylylsulfonyl) carbamate by reacting 2-phenylbenzene sulfonamide with diphenyl carbonate in the presence of a base and a polar solvent under an inert gas atmosphere. In such prior art process, use was made, as a polar solvent, of dimethylformamide and, as a base, of sodium hydride in the reaction that is further carried out under nitrogen gas atmosphere.

The reaction according to such prior art proceeds in relatively efficient manner, if it is carried out in a small scale reaction as carried out on a laboratory level. But if the reaction scale is made larger, the prior art process turns out to be disadvantageous in the yield and the purity of the product. Moreover, dimethylformamide is difficult to recover after the reaction and also sodium hydride is dangerous to handle, thus requiring utmost caution for the users (inflammability in moist air).

Therefore, the known process must be carried out under nitrogen gas atmosphere and thus can not involve a simple procedure, giving rise to complicated handling. Therefore, the known process poses various technical problems when it is attempted to carry it out on an industrial production scale.

It has been found that phenyl N-(2-biphenylylsulfonyl) carbamate of the formula (I)

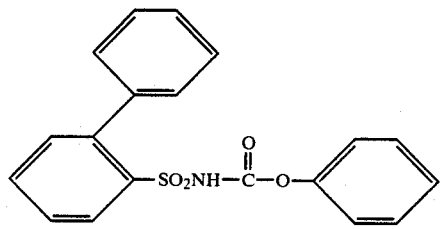

(I)

is obtained in high yield and purity by reacting 2-phenylbenzene sulfonamide

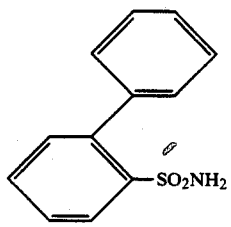

(II)

with diphenyl carbonate of the formula (III)

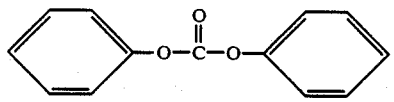

(III)

in the presence of an alkali metal hydroxide and an aprotic solvent at temperatures between about 20° C. and about 60° C., without using an inert gas atmosphere.

It is to be described as distinctly surprising that in carrying out the reaction according to the invention, the aimed product can be obtained with a high yield and purity, even if the reaction is carried out in an industrial production scale, while use may be made of not only easy-to-handle bases such as potassium hydroxide, sodium hydroxide etc., but also of easy-to-recover and reusable solvents such as toluene, xylene, acetonitrile etc., because in view of the prior art it was never expected that it would be possible to simplify and—at the same time—to essentially improve the troublesome prior art process in the points of purity, yield, base and solvent, even on an industrial scale production, which represent surprising advantages over the prior art.

The course of the reaction according to the invention can be represented by the following equation for instance:

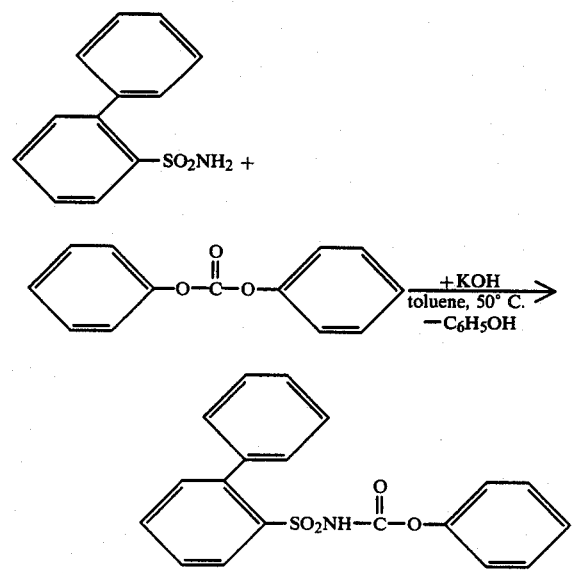

In the above process, use may be made, as the solvent, of aprotic, apolar solvents such as, for example, cyclohexane, toluene, xylene, methylene chloride, preferably toluene.

Further, acetonitrile may also be mentioned as the aprotic solvent, though it is of polar nature.

As alkali metal hydroxides to be used in the above process may be mentioned such as, for example, potassium hydroxide, sodium hydroxide and lithium hydroxide, preferably potassium hydroxide and sodium hydroxide.

The amount of the said alkali metal hydroxide used in the above-mentioned reaction may be the equi-molar amount (1 mol) to about 1.5 mols per mol of the starting material 2-phenylbenzene sulfonamide (II), preferably 1.05 mols to 1.2 mols alkali metal hydroxide per mol of (II).

The present process may be carried out at a reaction temperature of about 20° C. to about 60° C., preferably from about 30° C. to about 50° C., more preferably about 40° C. to about 50° C.

The present process may of course be carried out at normal pressure but it may also be carried out at an elevated or reduced pressure, though normal pressure is preferable.

In performing the process according to the invention, there are employed, per mol of 2-phenylbenzene sulfonamide (II), 1 to 1.5 mols of diphenyl carbonate (III) in either an aprotic, apolar solvent such as toluene or an aprotic, polar solvent such as acetonitrile, in the presence of an alkali metal hydroxide (in the equi-molar amount to about 1.5 mols per mol of 2-phenylbenzene sulfonamide (II)) at temperatures of about 20° C. to about 60° C., and then the reaction product is filtered to recover the solvent, followed by dissolution of the reaction residue in water and the subsequent acidification of such aqueous solution by the addition of hydrochloric acid to obtain the desired phenyl N-(2-biphenylylsulfonyl) carbamate (I).

Phenyl N-(2-biphenylylsulfonyl) carbamate prepared by the process according to the present invention is preferably used as an intermediate material for the production of herbicidally active compounds, such as, for example, N-2-biphenylylsulfonyl N'-(4,6-dimethoxy-1,3,5-triazin-2-yl) urea (see EP-A-56969).

The technical content of the present invention will be concretely described by way of the following examples but the present invention should not be taken as being restricted thereby in any reason.

EXAMPLE 1

2.33 kg (10 mols) of 2-phenylbenzene sulfonamide (II), 0.59 kg (10.5 mols) of potassium hydroxide and 2.14 kg (10 mols) of diphenyl carbonate (III) were introduced into 30 l of toluene and reacted under stirring for about six hours at 50° C., so as to produce the potassium salt of the desired product. Upon the completion of the reaction, the reaction product was cooled and filtered under suction.

The crystals thereby obtained were dissolved in water and the solution was acidified by the addition of hydrochloric acid thereto, to precipitate the desired phenyl N-(2-biphenylylsulfonyl) carbamate (I). The precipitated product was extracted with methylene chloride and the resulting organic phase was washed with water a few times, dried with sodium sulfate, and then subjected to distillation under reduced pressure to remove the methylene chloride therefrom, to obtain 3.4 kg of the desired phenyl N-(2-biphenylylsulfonyl) carbamate (I), having m.p. of 115°–118° C.

The yield, purity and net yield were 96%, 95% and 90.6%, respectively.

COMPARATIVE EXAMPLE 1 (according to JP-Application No. 70909/1984)

To 20 l of dried dimethyl formamide there were added 0.252 kg (10.5 mols) of sodium hydride under a nitrogen gas stream, followed by addition thereto of 5 l solution of 2.33 kg (10 mols) of 2-phenylbenzene sulfonamide (II) in dimethylformamide at a temperature not higher than 10° C. The reaction product was stirred for one hour followed by the addition thereto of 2.14 kg (10 mols) of diphenyl carbonate (III) at room temperature with further one hour stirring at room temperature.

Then, after the whole volume of the reaction mixture was added to ice water, it was acidified with hydrochloric acid, extracted with ethyl acetate and the resulting organic phase was dried, followed by the ethyl acetate being distilled therefrom, to obtain 2.4 kg of phenyl N-(2-biphenylylsulfonyl) carbamate (I).

The yield, purity and net yield obtained were 68%, 81% and 55.1%, respectively.

In the following table there are shown the results of the reactions according to the process of the present invention where the reaction conditions were varied, while use was made of the same procedure as described in Example 1:—see Examples 2–5, Example 6 being a further comparative example showing the use of a higher reaction temperature (70° C.).

TABLE

| Example No. | reactants (II) + (III) | base | solvent | reaction temperature and reaction time | amount of product (I) | yield (I) | purity (I) | net yield (I) |
|---|---|---|---|---|---|---|---|---|
| 2 (The present invention) | 2-diphenylbenzene sulfonamide 2.33 kg (10 mols) diphenylcarbonate 2.14 kg (10 mols) | potassium hydroxide 0.59 kg (10.5 mols) | acetonitrile | 40° C./6 hours | 3.3 kg | 93.5% | 95% | 88.8% |
| 3 (The present invention) | 2-phenylbenzene sulfonamide 2.33 kg (10 mols) diphenylcarbonate 2.57 kg (12 mols) | sodium hydroxide 0.48 kg (12 mols) | toluene | 50° C./5 hours | 3.4 kg | 96% | 96% | 92.2% |
| 4 (The present invention) | 2-phenylbenzene sulfonamide 2.33 kg (10 mols) diphenylcarbonate 3.21 kg (15 mols) | potassium hydroxide 0.6 kg (10.7 mols) | toluene | 50° C./5 hours | 3.2 kg | 90.7% | 91% | 82.5% |
| 5 (The present invention) | 2-phenylbenzene sulfonamide 2.33 kg (10 mols) diphenylcarbonate 2.57 kg (12 mols) | potassium hydroxide 0.59 kg (10.5 mols) | xylene | 50° C./6 hours | 3.4 kg | 96% | 95% | 90.6% |
| 6 Comparative example | 2-phenylbenzene sulfonamide 2.33 kg (10 mols) diphenylcarbonate 2.14 kg (10 mols) | potassium hydroxide 0.59 kg (10.5 mols) | toluene | 70° C./5 hours | trace amount | <10% | — | — |

It is understood that the specification and examples are illustrative but not limitative of the present invention and that other embodiments within the spirit and scope of the invention will suggest themselves to those skilled in the art.

We claim:

1. In the production of phenyl N-(2-biphenylylsulfonyl) carbamate of the formula

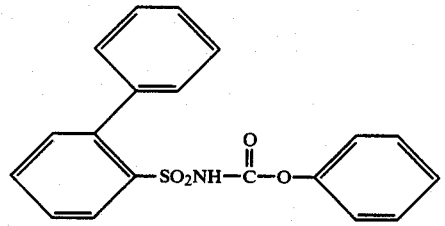

by reacting 2-phenylbenzene sulfonamide of the formula

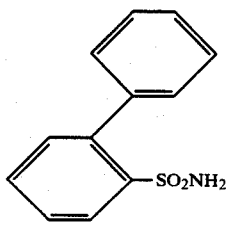

with diphenyl carbonate of the formula

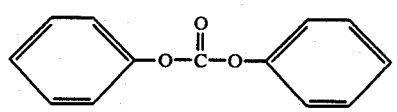

in the presence of a base and a solvent, the improvement which comprises effecting the reaction in the presence of an alkali metal hydroxide and an aprotic solvent at a temperature between about 20° C. and about 60° C.

2. The process according to claim 1, wherein said alkali metal hydroxide is potassium hydroxide or sodium hydroxide.

3. The process according to claim 1, wherein said apotic solvent is an apolar solvent.

4. The process according to claim 1, wherein said aprotic solvent is a member selected from the group consisting of cyclohexane, toluene, xylene and methylene chloride.

5. The process according to claim 1, wherein said aprotic solvent is toluene.

6. The process according to claim 1, wherein said aprotic solvent is acetonitrile.

7. The process according to claim 1, wherein the reaction temperature is about 30° C. to about 50° C.

8. The process according to claim 1, wherein the reaction temperature is about 40° C. to about 50° C.

9. The process according to claim 1, wherein there are employed 1 to 1.5 mols of diphenyl carbonate and 1 to 1.5 mols of alkali metal hydroxide per mol of 2-phenylbenzene sulfonamide.

10. The process according to claim 2, wherein said aprotic solvent is toluene or acetonitrile, the reaction temperature is about 40° C. to about 50° C., and about 1.05 to 1.2 mols of alkali metal hydroxide are employed per mol of sulfonamide.

* * * * *